United States Patent
Brunner

(10) Patent No.: US 8,181,649 B2
(45) Date of Patent: May 22, 2012

(54) TUBE SYSTEM FOR VENTILATION APPLIANCES

(75) Inventor: Josef Brunner, Chur (CH)

(73) Assignee: Hamilton Medical AG, Bonaduz (CH)

( * ) Notice: Subject to any disclaimer, the term of this patent is extended or adjusted under 35 U.S.C. 154(b) by 919 days.

(21) Appl. No.: 12/097,734

(22) PCT Filed: Nov. 9, 2006

(86) PCT No.: PCT/CH2006/000631
§ 371 (c)(1),
(2), (4) Date: Sep. 15, 2008

(87) PCT Pub. No.: WO2007/068132
PCT Pub. Date: Jun. 21, 2007

(65) Prior Publication Data
US 2009/0050153 A1 Feb. 26, 2009

(30) Foreign Application Priority Data

Dec. 16, 2005 (CH) ..................................... 1993/05

(51) Int. Cl.
*F16K 31/02* (2006.01)
(52) U.S. Cl. .......... 128/204.23; 128/204.21; 128/204.18
(58) Field of Classification Search . 128/200.18–205.25
See application file for complete search history.

(56) References Cited

U.S. PATENT DOCUMENTS

| 3,964,476 A | 6/1976 | Palleni |
| 4,083,245 A | 4/1978 | Osborn |
| 5,492,115 A * | 2/1996 | Abramov et al. ........ 128/205.24 |
| 5,647,351 A * | 7/1997 | Weismann et al. ...... 128/204.21 |
| 5,660,171 A * | 8/1997 | Kimm et al. ............. 128/204.23 |
| 6,119,686 A * | 9/2000 | Somerson et al. ....... 128/202.22 |
| 6,152,129 A | 11/2000 | Berthon-Jones |
| 6,203,502 B1 * | 3/2001 | Hilgendorf et al. ........... 600/538 |
| 6,230,708 B1 * | 5/2001 | Radko ...................... 128/205.24 |
| 6,269,811 B1 * | 8/2001 | Duff et al. ................ 128/204.21 |
| 7,100,607 B2 * | 9/2006 | Zdrojkowski et al. ... 128/204.18 |
| 2005/0087190 A1 | 4/2005 | Jafari |
| 2006/0000475 A1 * | 1/2006 | Matthews et al. ........ 128/204.21 |
| 2006/0249150 A1 | 11/2006 | Dietz et al. |

FOREIGN PATENT DOCUMENTS

| FR | 2 249 650 | 5/1975 |
| WO | WO 98/06449 | 2/1998 |
| WO | WO 03/033175 | 4/2003 |
| WO | WO 03/055552 | 7/2003 |
| WO | WO 2004/084980 | 10/2004 |

* cited by examiner

*Primary Examiner* — Justine Yu
*Assistant Examiner* — Rachel Young
(74) *Attorney, Agent, or Firm* — Morriss O'Bryant Compagni, P.C.

(57) ABSTRACT

The invention relates to a three-arm tube system for a ventilation appliance suitable for invasive ventilation. Such a ventilation appliance includes an active inhalation valve and an active exhalation valve. The tube system also includes an inhalation tube arm, an exhalation tube arm and a ventilation tube arm for attachment to a mask, and also a flow sensor. A defined leakage is established in the ventilation tube arm, and the flow sensor is arranged between the leakage and the mask. The invention further relates to a ventilation appliance having such a tube system, and to a method for operating the ventilation appliance.

27 Claims, 2 Drawing Sheets

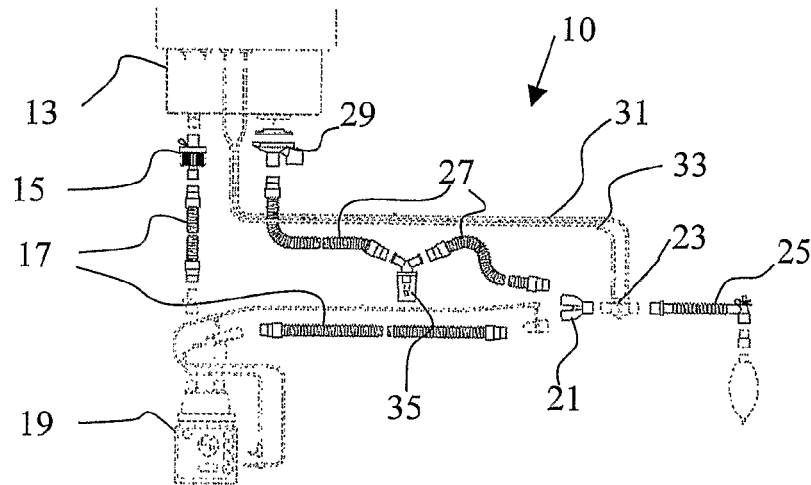
Prior Art  Fig. 1
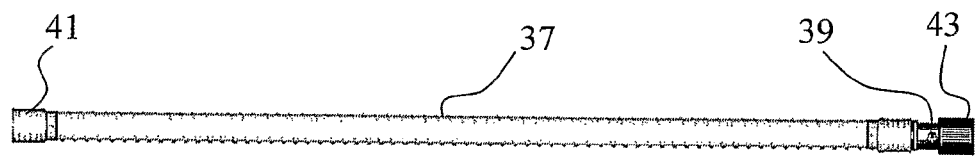
Prior Art  Fig. 2
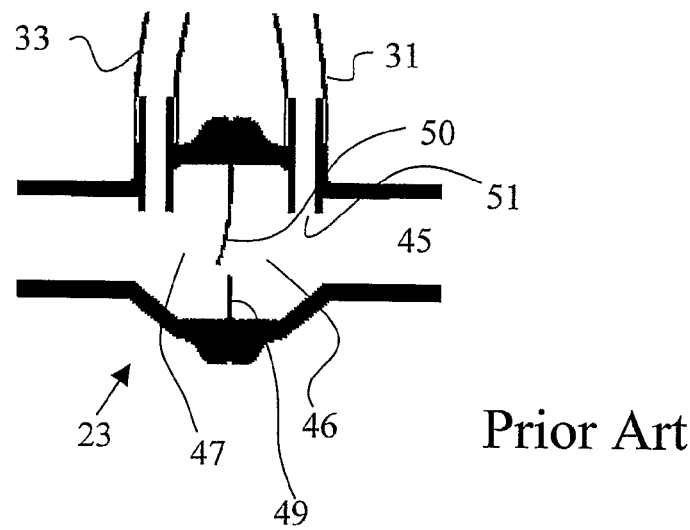
Prior Art  Fig. 3

TUBE SYSTEM FOR VENTILATION APPLIANCES

This application claims priority to International Application PCT/CH2006/000631 filed Nov. 9, 2006 and Swiss Patent Application No. 1993/05 filed on Dec. 16, 2005, the entirety of which is incorporated by reference.

SCOPE OF THE INVENTION

The invention relates to a tube system for ventilation appliances, a ventilation appliance having such a tube system, a method for operating a ventilation appliance, and a method for the mechanical ventilation of patients.

PRIOR ART

Dual tube systems are utilized for invasive ventilation. Dual tube systems have an inhalation tube and an exhalation tube that are connected to the patient mask via a Y piece. The inhalation tube is subsequently connected to an inhalation filter protecting the ventilation appliance from contamination. A moisturizing device is possibly arranged between an inhalation tube piece on the device side and an inhalation tube piece on the patient side. On the patient side of the Y piece a flow sensor may be arranged, and a tubus via an intermediate tube.

The exhalation tube connecting the Y piece feeds the breathing air back to the ventilation appliance, and may be equipped with a water trap. The ventilation appliance has an inhalation valve and an exhalation valve, each actively being activated. For inhalation the exhalation valve is closed and the inhalation valve is opened in order to obtain an over pressure in the lungs and in the tubes. For exhaling the exhalation valve is opened and the inhalation valve is closed in order to ensure exhalation having as little resistance as possible. Due to the active control of the inhalation valve and the exhalation valve an endexspiratory pressure may also be dosed.

In order to determine the actual ventilation volume in dual tube system, and to determine the patient's own activity, the applicant connects a flow sensor between the Y piece and the mask according to U.S. Pat. No. 4,083,245.

For the non-invasive mechanical ventilation single tube system (single limb breathing systems) are utilized. Single tube systems are characterized by a single ventilation tube that connects to an inhalation filter protecting the ventilation appliance against contamination, and which bridges the distance between the ventilation appliance and the patient, and by a mask. There are closed and open single tube systems. Closed single tube systems have an active exhalation valve that is often controlled by the ventilation appliance via an air pressure line. It is positioned in the ventilation tube on the patient side. The system is often equipped with a pressure measuring tube, by means of which a pressure of the ventilation air or of the exhalation air can be measured at the exhalation valve in order to be able to calculate the effective ventilation of a patient. An intermediate tube may be present between the exhalation valve and the mask so that the exhalation valve is not arranged directly in front of the patient's face. The patient is ventilated by the ventilation appliance through the ventilation tube. When the patient inhales the exhalation valve is in an inhalation position, in which an over pressure that is present in the tube reaches the mask and the patient's lungs. An exhalation opening is closed so that the desired over pressure of the ventilation air in the mask can build up. When exhaling the exhalation valve is in an exhalation position, in which a connection between the tube and the mask is closed, but in which the exhalation air can escape through the exhalation opening at a resistance that is as low as possible. Such single tube systems are practically equal to dual tube system. They differ from dual tube systems practically only in that the exhalation valve is arranged near the patient, thus are removed from the ventilation appliance.

Such single tube systems have the disadvantage that the weight hanging from the mask and the presence of the exhalation valve on the patient side are bothersome for the patient.

In order to overcome this disadvantage, an open single tube systems exists, which omit an active exhalation valve. The ventilation tube of such an open system has a predetermined leakage. This leakage is defined by a hole in the ventilation tube, which hole has a selected cross-section. This leakage is embodied on the end of the tube on the patient side. The exhalation air escapes through this opening. The fresh ventilation air also partially escapes through this hole. For this reason, more ventilation air in such ventilation systems must be prepared and fed through the tube, than the patient requires. In order to calculate the necessary amount of ventilation air, the pressure in the tube with this leakage is measured, or a mathematical approximation is carried out based on the characteristics established by the manufacturer and distinguishing the tube system. These open single tube systems are pleasant for the patient, because the patient merely has a single tube and the mask placed on. The patient is free to exhale at any time, even against the pressure of the ventilation appliance, and can inhale at any time, even if the ventilation appliance supplies no ventilation air.

In open single tube systems the pressure in the ventilation tube is rapidly released through the ventilation appliance during exhaling. In this manner, an exhalation of the patient with as little resistance as possible is enabled. For this purpose, exhausted exhalation air flows into the ventilation tube. Shortly before completion of the exhalation time, the ventilation pressure in the ventilation tube is replenished. During the breathing pause until the next inhalation, the exhalation air present in the tube is therefore pressed out through the leakage, and the tube is thereby flushed.

Therefore, with a changeover from invasive to non-invasive ventilation a change is usually made from a dual tube system to an open or closed single tube system in order to remove the burden of a heavy dual tube system from the patient. However, since ventilation appliances for invasive ventilation depend on the fact that the exhalation tube is connected to the exhalation valve in order to control the ventilation pressure in the tube and in the lungs, it has been required to also change the ventilation appliance along with the tube system.

OBJECT OF THE INVENTION

It is therefore the object of the present invention to enable the use of a ventilation appliance equipped for the invasive ventilation, having an active inhalation valve and an active exhalation valve, for the non-invasive ventilation, having a tube system that is pleasantly light-weight for the patient, particularly a commercially available tube of a single tube system.

SOLUTION OF THE OBJECT

This object is solved according to the invention by means of the characteristics of claim 1.

Accordingly, a three-arm, e.g. a tube system embodied in a Y shape, for a ventilation appliance suitable for invasive ventilation, is embodied having an active inhalation valve and an active exhalation valve, having an inhalation tube arm for connection to the inhalation valve of the ventilation appliance, an exhalation tube arm for connection to the exhalation valve of the ventilation appliance, and a ventilation tube arm for connection to a mask or to a tubus. It further has a flow sensor, which is arranged, or is to be arranged on the ventilation tube arm for measuring the inhalation volume and the exhalation volume. According to the invention a defined leakage is embodied in this tube system in the ventilation tube arm, and the flow sensor is arranged, or is to be arranged between this leakage and the mask or the tubus.

The leakage enables the embodiment of the ventilation tube arm with a large volume, e.g. having a large length. In this manner a single tube can be connected to the mask or to the tubus so that the patient feels as if he/she were connected to an open single tube system. The patient does not have to put up with a cumbersome exhalation valve near the patient, or with two tubes. The tube system is divided into the inhalation tube arm and the exhalation tube arm only near the appliance.

The leakage has the advantage that the patient can breathe, even if the appliance does not supply any ventilation air for any reason. The patient can also resist the mechanical ventilation at any time. In this case, the ventilation air simply flows through the leakage. The patient can also exhale at any time, even with a closed exhalation valve. This freedom of the patient reduces the restricting feeling of mechanical ventilation. Due to the leakage the ventilation tube is flushed before each inhalation phase. The exhaled air present in the ventilation tube is pressed out through the leakage. Practically the entire contents of the ventilation tube has flowed out of the same until the ventilation pressure has been reached, with which the patient's lungs are filled. Therefore, the lungs are filled with fresh ventilation air.

Modern ventilation appliances have algorithms, due to which the amount of air to be supplied, the pressure to be supplied, and the breathing frequency can be calculated based on the parameters measured using the flow sensor. Any losses due to an undetermined and/or the defined leakage are compensated by the ventilation appliance.

The connection of the open ventilation tube to an exhalation valve via an exhalation tube arm enables a rapid exhalation with as little resistance as possible.

Purposefully, the tube system is interconnected. In this case the components include an inhalation tube, or an inhalation tube kit, an exhalation tube, or an exhalation tube kit, a Y piece, a ventilation tube, or a ventilation tube kit of an open single tube system, and the flow sensor. Possibly, the tube system includes a connection tube between the flow sensor and the mask or tubus.

The flow sensor is advantageously comprised of a housing having a gas inlet nozzle and a gas outlet nozzle, in which the interior space of the housing is divided into two zones between the inlet nozzle and the outlet nozzle by means of a baffle membrane. A pressure measuring device or a connection to a pressure measuring device is present in each of these zones. The baffle membrane is advantageously comprised of an elastic material. It has an opening and a damper embodied as one piece along with the baffle membrane, which corresponds in shape and size to the opening, and which is connected to the baffle membrane in the manner of a hinge. The edge of the opening advantageously extends divergently away from the hinge-type connection, and has a directional change at a distance to the hinge-type connection in order to form a point of the lowest width of the opening as opposed to the hinge-type connection. The damper is purposefully embodied in a manner pivoting about the hinge-type connection, and can be pivoted in front of the pressure measuring opening ending in the zone on the outflow side in case of a high gas throughput.

The only damper has an elasticity, and the only opening has a shape ensuring that the resistance of the opening is constant across a large throughput range.

Such flow sensors are known, and are successfully utilized by the applicant in conventional dual tube systems.

A ventilation appliance suitable for invasive ventilation has an active inhalation valve, and typically an active exhalation valve, and requires a three-arm tube system for the Y-shaped connection of the inhalation valve, the patient, and the exhalation valve. It is known to equip such tube systems with a flow sensor to be arranged near the patient. However, such a ventilation appliance, having a tube system, is now characterized in a novel manner in that a defined leakage is present in a ventilation tube arm directed toward the patient, and that the flow sensor is arranged between the leakage and a mask, or a tubus. The advantages of this leakage are described above.

The ventilation appliance is operated accordingly in a novel manner. The ventilation air is supplied to a ventilation tube and a ventilation mask, or a tubus, on the patient side in a known manner via an actively controlled inhalation valve and an inhalation tube. The exhalation air is released at least partially, also in a known manner, via the ventilation tube, an exhalation tube, and an actively controlled exhalation valve. The breathing frequency and the breathing volume are monitored by means of a flow sensor on the patient side. The breathing pressure, endexspiratory pressure, breathing frequency, and volume of the breathing air, among others, are controlled based on the parameters provided by the flow sensor. With this control any leakages possibly present in the tube system are determined as to their quantity by means of a flow measuring in the ventilation appliance, and by means of the flow measurement by means of the flow sensor on the patient side, and compensated by means of the ventilation appliance. It is also novel that a defined leakage is provided in the ventilation tube on the side of the flow sensor facing away from the patient. With the method according to the invention the ventilation appliance equipped with an exhalation valve presses out any gas present in the ventilation tube from the tube system during the breathing pause between the end of the exhalation phase and the beginning of the inhalation phase by means of the leakage.

For the mechanical ventilation of a patient using a ventilation appliance suitable for invasive ventilation, the breathing frequency, the breathing pressure, the endexspiratory pressure, and the breathing volume are monitored in a known manner using a flow sensor on the patient side. Due to the parameters detected by the flow sensor, and by using the gas mixer, the inhalation valve, and the exhalation valve, the breathing pressure, the breathing volume, and the endexspiratory pressure are controlled in a patient-oriented manner. Any leakages possibly present are compensated, in that the gas mixer, the inhalation valve, and the exhalation valve are actively controlled. However, if a defined leakage is provided in the ventilation tube arm according to the invention on the side facing away from the patient of the flow sensor near the patient, the exhalation air is partially blown out by this leakage before the patient's lungs are filled with fresh ventilation air. This has the advantage that a known single tube system having a ventilation appliance configured for dual tube systems can be used, and the patient can therefore be changed over from an invasive to a non-invasive ventilation without changing appliances.

BRIEF DESCRIPTION OF THE FIGURES

FIG. 1 schematically illustrates the known prior art regarding dual tube systems for invasive ventilation appliances.

FIG. 2 schematically illustrates the known prior art regarding open single tube systems.

FIG. 3 schematically illustrates the prior art regarding the flow sensor.

DETAILED DESCRIPTION OF THE EXEMPLARY EMBODIMENTS ILLUSTRATED IN THE FIGURES

Prior Art

Figure 4:
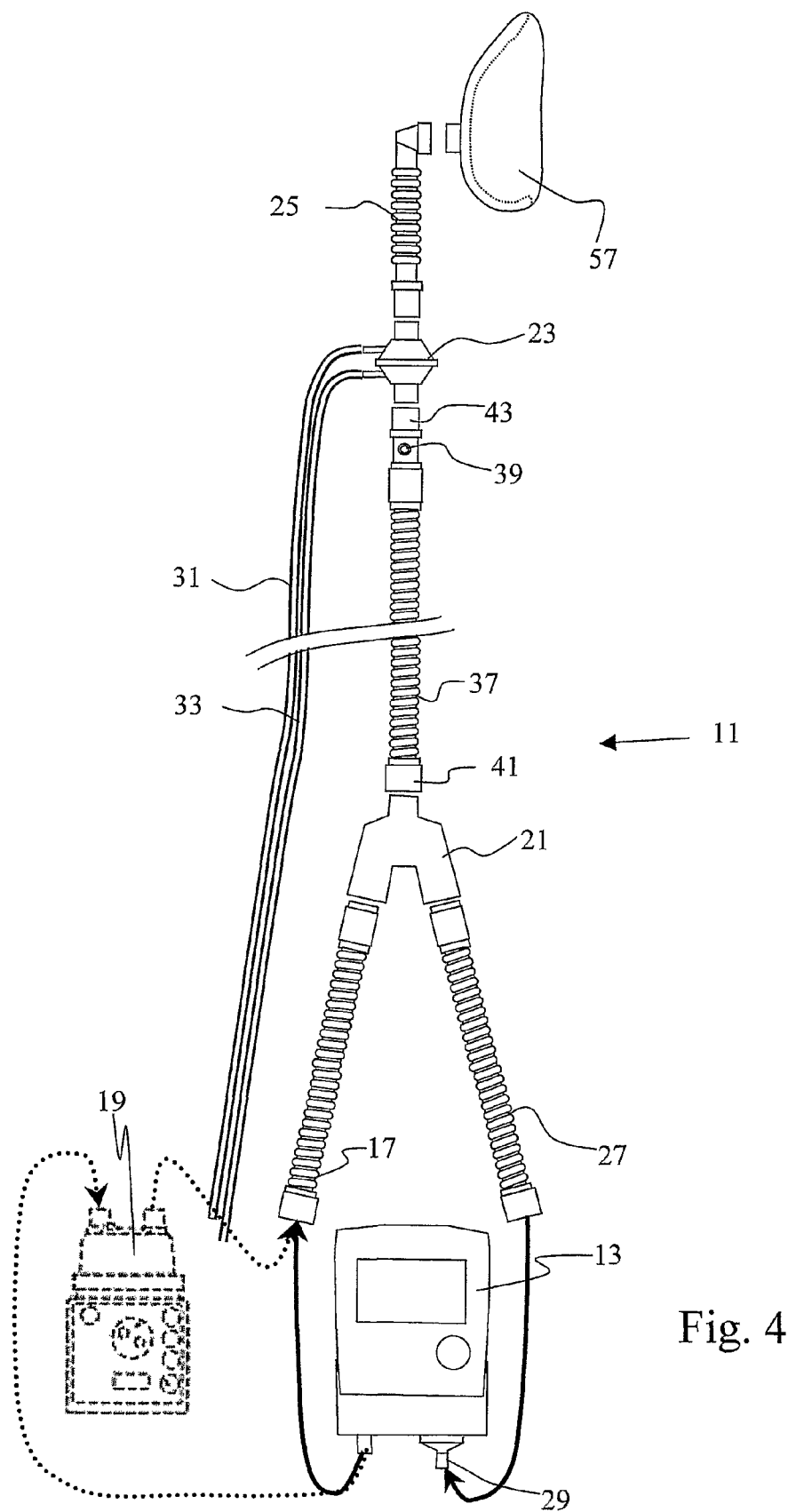
FIG. 4 schematically illustrates the tube system according to the invention.

As described above, prior art includes single tube systems and dual tube systems. The known dual tube system illustrated in FIG. 1 is suitable and configured for invasive ventilation. This dual tube system is therefore to be connected to a ventilation appliance 13 that is suitable for the invasive ventilation. Such an invasive ventilation appliance 13 has two actively controlled valves, namely the inhalation valve (not illustrated, as it is arranged in the interior of the appliance), and the exhalation valve 29. An inhalation tube kit 17 connected to an appliance outlet via a filter 15, and an exhalation tube kit 29 connected to the exhalation valve 29, are connected to a Y piece 21 on their ends facing away from the ventilation appliance 13. The Y piece 21 gathers the two tubes 17 and 27, and combines the same to a single tube 25 leading to the patient. A flow sensor 23 is arranged on the Y piece on the patient side. The flow sensor 23 is connected to the ventilation appliance 13 via two air lines 31, 33. Accessories may be interconnected in the tube kits 17 and 27. Purposefully, a moisturizing device 19 is connected to the inhalation tube 17. Purposefully, a water trap 35 is provided in the exhalation tube 27. The breathing air of the patient flows only within the connection tube 27 and the flow sensor 23 in both directions. The contents of the connection tube 25 and of the flow sensor 23 must therefore flow into any calculation of the required breathing volume as a serial dead space.

Ventilation tubes 37 are used in open single tube systems. Such a known ventilation tube 37 (FIG. 2) is flowed through by the breathing air in both directions across its entire length. So that this ventilation tube 37 does not form a very large serial dead space, it has a leakage 39. Practically the entire exhausted breathing air flows out through the leakage when exhaling, and during the breathing pause after exhaling, namely until the required breathing pressure has been restored. However, part of the fresh breathing air also flows out from the leakage 39. It is critical with the setting up of the ventilation tube 37 between the patient and the ventilation appliance to ensure that the leakage is near the patient in order to keep the serial dead space as low as possible. The end 41 of the ventilation tube 37 farthest from the leakage must therefore be connected to the ventilation appliance; the end 43 near the leakage must be connected either directly, or via a connection tube 27, to a mask. Such open ventilation systems are currently being used only for the non-invasive mask ventilation. Until now it was deemed impossible to connect one tube of a single tube system to a device for a dual tube system.

FIG. 3 illustrates a schematic section across the known flow sensor 23. The flow sensor 23 has an inlet nozzle 45, a first chamber 46, a second chamber 47, and an outlet nozzle in a housing. The first and second chambers 46, 47 are separated by means of a membrane 49. This membrane 49 has an opening, and a damper 50 filling out the opening. The damper 50 is embodied in a pivoting manner like a swing-door so that it may protrude into the one or into the other chamber, depending on which direction the breathing air flow is directed. The flow sensor 23 is embodied symmetrically so that it can measure the pressure drop in both directions, which occurs as a result of the flowing through of the breathing air through the opening. The pressures in the chambers are supplied to the ventilation appliance via the air tubes 31, 33, and are measured in the ventilation appliance. Due to this pressure drop the ventilation appliance can calculate the pressure ratios in the breathing are, and the ventilation volume. These calculations are very significant practically irrespective of how large a leakage is between the flow sensor and the ventilation appliance 13.

EXEMPLARY EMBODIMENT ACCORDING TO THE INVENTION

FIG. 4 illustrates the tube system 11 according to the invention. The components are known. The composition, however, is novel, and has critical advantages. The inhalation tube 17 and the exhalation tube 27 are short pieces of tubes, such as are used, for example, in the tube system 10 according to FIG. 1 between the filter 15 and the moisturizing device 19. Their length must simply allow that both tubes can be connected at their one ends to the ventilation appliance. A moisturizing device 19 may also be provided in this area between the ventilation appliance 13 and the Y piece. The Y piece, which gathers the two tubes 17 27 on the appliance side and combines them with the ventilation tube 37, may be identical to the previously known Y piece. The ventilation tube 37 connected to the same is a tube according to FIG. 2, and is also known. The flow sensor 23, which is arranged on the ventilation tube 37 on the patient side, is also known. The composition according to the invention of known ventilation tube components is characterized in that a Y-shaped tube system is formed, having two preferably short arms 17, 27, which can be connected to an invasive ventilation appliance 13. The third arm is a long ventilation tube 37 having a defined leakage 39 provided on the patient side. Further, a flow sensor 23, and purposefully, a connection tube 25 are connected to the ventilation tube. A mask 57, but also a tubus in certain circumstances, can be arranged on the connection tube 25.

A filter 15 may be provided for the protection of the ventilation appliance. This filter can be provided between the appliance 13 and the inhalation tube 17.

This tube system 11 has critical advantages as opposed to the known tube systems:

With this tube system according to the invention an appliance configured the invasive ventilation may also be utilized for the non-invasive ventilation.

With a changeover from invasive to non-invasive ventilation, the dual tube system, having the tubus, merely needs to be exchanged with a Y tube system according to the invention, having a mask.

With a changeover from non-invasive to invasive ventilation, quick action can be taken, since the ventilation appliance is already suitable for an invasive ventilation.

Standard components may be utilized.

With a non-invasive ventilation the tube system is minimal with regard to weight and obstruction to the patient.

With a non-invasive ventilation, the tube system allows a maximum of freedom of movement, freedom of breathing, safety in case of malfunctions, minimum exhalation resistance, and maximum control by means of close patient monitoring.

The defined leakage (39) does not require to be monitored by means of a maneuver, since the proximal flow sensor (23) measures the actual discharged breathing volume, and automatically compensates the leakage within the tube system.

Calibration of the flow sensor can be carried out in a conventional manner, wherein the leakage must be closed during the calibration maneuver, for example, by means of a finger pressed onto the opening.

The invention claimed is:

1. A three-arm tube system for a ventilation appliance suitable for invasive ventilation, wherein the ventilation appliance comprises an active inhalation valve and an active exhalation valve comprising:
   an inhalation tube arm configured for connecting to an inhalation valve of a ventilation appliance;
   an exhalation tube arm configured for connecting to the exhalation valve of the ventilation appliance;
   a ventilation tube arm configured for connecting on a patient side to a mask or a tubus;
   a flow sensor configured to be arranged on the ventilation tube arm for measuring an inhalation volume and an exhalation volume; and
   a defined leakage in the ventilation tube arm;
   the flow sensor configured to be arranged between the leakage and the mask, or the tubus.

2. The tube system according to claim 1, wherein the tube system comprises at least one of an inhalation tube, an inhalation tube set, an exhalation tube, an exhalation tube set, a Y piece, a ventilation tube, a ventilation tube set of an open one-tube system, a flow sensor, a connecting tube, mask and tubus.

3. The tube system according to claim 1, wherein the flow sensor is comprised of a housing having a gas inlet nozzle and a gas outlet nozzle, the interior of the housing divided into two zones of the inlet nozzle and the outlet nozzle by a baffle membrane, and a pressure measuring device, or a connection to a pressure measuring device at each of these zones.

4. The tube system according to claim 3, wherein the baffle membrane is comprised of an elastic material having an opening therein, and a one piece damper corresponding to the shape and size of the opening connected to the baffle membrane in the manner of a hinge-type connection.

5. The tube system according to claim 4, wherein an edge of the opening extends divergently away from the hinge-type connection and has a directional change at a distance to the hinge-type connection in order to form a point of the lowest width of the opening opposite to the hinge-type connection.

6. The tube system according to claim 3, wherein the damper pivots about the hinge-type connection, and can be pivoted in front of the opening ending in the zone on the outflow side in case of a high gas throughput.

7. The tube system according to claim 3, wherein a single damper and a single opening are included in the baffle membrane.

8. The tube system according to claim 4, wherein a shape and an elasticity of the damper is configured such that a resistance of the opening is constant across a large throughput range.

9. A ventilation appliance suitable for invasive ventilation, comprising:
   an active exhalation valve, an active inhalation valve, and a three-arm tube system for connecting the inhalation valve and the exhalation valve to a patient's mask, or a tubus;
   a flow sensor arranged adjacent to a patient in a ventilation tube arm; and
   a defined leakage in the ventilation tube arm directed toward the patient, the flow sensor arranged between the leakage and the mask, or the tubus.

10. A method for operating a ventilation appliance, comprising:
    supplying ventilation air to a ventilation tube and a ventilation mask adjacent to a patient's side, or to a tubus with a ventilation appliance via an actively controlled inhalation valve and an inhalation tube,
    releasing exhalation air via the ventilation tube, an exhalation tube, and an actively controlled exhalation valve,
    monitoring a breathing frequency and a breathing volume passing through the ventilation tube with a flow sensor on the patient's side of the ventilation tube,
    controlling a ventilation pressure, end expiratory pressure, ventilation frequency and volume of ventilation air based on parameters supplied by the flow sensor, wherein any leakages possibly present in the tube system are quantifiably determined by a flow quantity measurement in the ventilation appliance, and a flow quantity measurement by means of the flow sensor on the patient's side, and are compensated by the ventilation appliance,
    providing a defined leakage in the ventilation tube on a side of the flow sensor facing away from the patient, and
    exchanging any gas present in the ventilation tube with the ventilation appliance during a breathing pause between an end of an exhalation phase and a beginning of an inhalation phase by the leakage.

11. A method for the mechanical ventilation of a patient, having a ventilation appliance suitable for invasive ventilation, comprising:
    monitoring a breathing frequency, ventilation pressure, an end expiratory pressure and a ventilation volume with a flow sensor arranged in a ventilation tube on the patient's side, controlling the ventilation pressure, the ventilation volume, and the end expiratory pressure in a patient-oriented manner based on parameters detected by the flow sensor, and with a gas mixer of the ventilation appliance,
    compensating for any leakages present by actively controlling the gas mixer, the inhalation valve, and the exhalation valve
    providing a defined leakage in the ventilation tube adjacent to the patient, the defined leakage located on a side of the flow sensor facing away from the patient of the flow sensor in the ventilation tube adjacent to the patient, and
    partially releasing the exhalation air via the leakage.

12. The method of claim 11, further comprising using an open single tube system in conjunction with a Y piece, an inhalation tube, and an exhalation tube on the ventilation appliance, having an actively controlled inhalation valve and an actively controlled exhalation valve.

13. The method of claim 12, wherein the flow sensor is arranged on the single tube system adjacent to the patient.

14. The method of claim 10, further comprising using an open single tube system in conjunction with a Y piece, an inhalation tube, and an exhalation tube on the ventilation appliance, having an actively controlled inhalation valve and an actively controlled exhalation valve.

15. The method of claim 14, wherein the flow sensor is arranged on the single tube system adjacent to the patient.

16. The tube system according to claim 1, wherein the defined leakage is located near an end of the ventilation tube arm on the patient side.

17. The tube system according to claim 9, wherein the defined leakage is located near an end of the ventilation tube arm on the patient side.

18. The tube system according to claim 10, wherein the defined leakage is located near an end of the ventilation tube arm on the patient side.

19. The tube system according to claim 11, wherein the defined leakage is located near an end of the ventilation tube arm on the patient side.

20. A three-arm tube system for a ventilation appliance suitable for invasive ventilation, wherein the ventilation appliance comprises an active inhalation valve and an active exhalation valve comprising:
- an inhalation tube arm configured for connecting to an inhalation valve of a ventilation appliance;
- an exhalation tube arm configured for connecting to the exhalation valve of the ventilation appliance;
- a three-way-junction connecting the inhalation tube arm and the exhalation tube arm, and connecting the inhalation tube arm and the exhalation tube arm to a single ventilation tube arm, the ventilation tube arm configured for connecting on a patient side to a mask or a tubus;
- a flow sensor configured to be arranged on the ventilation tube arm for measuring an inhalation volume and an exhalation volume; and
- a defined leakage in the ventilation tube arm, the flow sensor configured to be arranged between the leakage and the mask or the tubus.

21. The tube system according to claim 20, wherein the defined leakage is located near an end of the ventilation tube arm on the patient side.

22. A ventilation appliance suitable for invasive ventilation, comprising:
- an active exhalation valve;
- an active inhalation valve;
- a three-arm tube system for connecting the inhalation valve and the exhalation valve to a three-way-junction and connecting the inhalation valve and the exhalation valve to a ventilation tube arm directed toward a patient's mask, or a tubus;
- a flow sensor arrangeable adjacent to a patient in the ventilation tube arm; and
- a defined leakage in the ventilation tube arm, the flow sensor arranged between the defined leakage and the mask, or the tubus.

23. The tube system according to claim 22, wherein the defined leakage is located near an end of the ventilation tube arm on the patient side.

24. A method for operating a ventilation appliance, comprising:
- supplying ventilation air to a ventilation tube and a ventilation mask adjacent to a patient's side, or to a tubus with a ventilation appliance via an actively controlled inhalation valve and an inhalation tube;
- releasing exhalation air via the ventilation tube, an exhalation tube, and an actively controlled exhalation valve, the inhalation tube and the exhalation tube connected in a Y-junction to the ventilation tube on a side of the ventilation tube facing away from the patient;
- monitoring a breathing frequency and a breathing volume passing through the ventilation tube with a flow sensor on the patient's side of the ventilation tube;
- controlling a ventilation pressure, end expiratory pressure, ventilation frequency and volume of ventilation air based on parameters supplied by the flow sensor
- providing a defined leakage in the ventilation tube on a side of the flow sensor facing away from the patient, and
- exchanging any gas present in the ventilation tube between the leakage and the three-way-junction with the ventilation appliance during a breathing pause between an end of an exhalation phase and a beginning of an inhalation phase by the leakage;
- wherein any leakages present in the tube system are quantifiably determined by a flow quantity measurement in the ventilation appliance and a flow quantity measurement by the flow sensor on the patient's side, and are compensated by the ventilation appliance.

25. The tube system according to claim 24, wherein the defined leakage is located near an end of the ventilation tube arm on the patient side.

26. A method for the mechanical ventilation of a patient, having a ventilation appliance suitable for invasive ventilation, comprising:
- monitoring a breathing frequency, ventilation pressure, an end expiratory pressure and a ventilation volume with a flow sensor arranged in a ventilation tube on the patient's side of a three-way-junction with an inhalation tube and an exhalation tube;
- controlling the ventilation pressure, the ventilation volume, and the end expiratory pressure in a patient-oriented manner based on parameters detected by the flow sensor;
- compensating for any leakages present by actively controlling a gas mixer, the inhalation valve, and the exhalation valve;
- providing a defined leakage in the ventilation tube adjacent to the patient, the defined leakage located on a side of the flow sensor facing away from the patient and on a side of the three-way-junction facing toward the patient; and
- partially releasing the exhalation air via the leakage.

27. The tube system according to claim 26, wherein the defined leakage is located near an end of the ventilation tube arm on the patient side.

* * * * *